(12) United States Patent
Furrer

(10) Patent No.: US 8,664,261 B2
(45) Date of Patent: Mar. 4, 2014

(54) ORGANIC COMPOUNDS HAVING COOLING PROPERTIES

(75) Inventor: Stefan Michael Furrer, Cincinatti, OH (US)

(73) Assignee: Givaudan S.A., Vernier (CH)

( * ) Notice: Subject to any disclaimer, the term of this patent is extended or adjusted under 35 U.S.C. 154(b) by 13 days.

(21) Appl. No.: 13/266,532

(22) PCT Filed: May 4, 2010

(86) PCT No.: PCT/EP2010/055999
§ 371 (c)(1),
(2), (4) Date: Dec. 8, 2011

(87) PCT Pub. No.: WO2010/128026
PCT Pub. Date: Nov. 11, 2010

(65) Prior Publication Data
US 2012/0095042 A1    Apr. 19, 2012

Related U.S. Application Data

(60) Provisional application No. 61/175,513, filed on May 5, 2009.

(51) Int. Cl.
*A01N 43/38* (2006.01)
*A61K 31/405* (2006.01)
*C07D 209/04* (2006.01)

(52) U.S. Cl.
USPC .......................................... 514/415; 548/469

(58) Field of Classification Search
None
See application file for complete search history.

(56) References Cited

U.S. PATENT DOCUMENTS

| | | | |
|---|---|---|---|
| 4,153,679 A | 5/1979 | Rowsell et al. | |
| 6,039,901 A | 3/2000 | Soper et al. | |
| 6,045,835 A | 4/2000 | Soper et al. | |
| 6,106,875 A | 8/2000 | Soper et al. | |
| 6,325,951 B1 | 12/2001 | Soper et al. | |
| 6,335,047 B1 | 1/2002 | Daniher et al. | |
| 6,348,625 B1 | 2/2002 | Anderson | |
| 6,440,912 B2 | 8/2002 | McGee et al. | |
| 6,451,366 B1 | 9/2002 | Daniher et al. | |
| 6,482,433 B1 | 11/2002 | DeRoos et al. | |
| 6,689,740 B1 | 2/2004 | McGee et al. | |
| 7,414,152 B2 | 8/2008 | Galopin et al. | |
| 2002/0081370 A1 | 6/2002 | Daniher et al. | |
| 2005/0187211 A1* | 8/2005 | Wei | 514/223.8 |
| 2005/0214337 A1 | 9/2005 | McGee et al. | |
| 2005/0233042 A1 | 10/2005 | Galopin et al. | |
| 2006/0035008 A1 | 2/2006 | Virgallito et al. | |
| 2006/0051301 A1 | 3/2006 | Galopin et al. | |
| 2006/0172917 A1 | 8/2006 | Vedantam et al. | |
| 2006/0276667 A1 | 12/2006 | Galopin et al. | |
| 2008/0112899 A1 | 5/2008 | Galopin et al. | |
| 2008/0311266 A1 | 12/2008 | Gray et al. | |
| 2008/0319055 A1 | 12/2008 | Cole et al. | |
| 2009/0030042 A1 | 1/2009 | Furrer et al. | |
| 2009/0105237 A1 | 4/2009 | Bell et al. | |
| 2010/0035938 A1 | 2/2010 | Bell et al. | |
| 2010/0297038 A1 | 11/2010 | Furrer et al. | |
| 2011/0182833 A1 | 7/2011 | Furrer et al. | |

FOREIGN PATENT DOCUMENTS

| | | |
|---|---|---|
| AU | 7593174 | 3/1976 |
| DE | 24 58 562 A1 | 6/1975 |
| FR | 2127013 | 10/1972 |
| GB | 1 351 761 A | 5/1974 |
| GB | 1 421 744 A | 1/1976 |
| GB | 1 457 671 A | 12/1976 |
| GB | 1 502 706 A | 3/1978 |
| WO | WO 01/03825 A | 1/2001 |
| WO | WO 2005/002582 A1 | 1/2005 |
| WO | WO 2005/020897 A2 | 3/2005 |
| WO | WO 2005/049553 A1 | 6/2005 |
| WO | WO 2006/056096 A | 6/2006 |
| WO | WO 2006/092076 A | 9/2006 |

(Continued)

OTHER PUBLICATIONS

International Preliminary Report on Patentability, issued on Nov. 9, 2011, for the corresponding PCT International patent application No. PCT/EP2010/055999.

(Continued)

*Primary Examiner* — Jeffrey S. Lundgren
*Assistant Examiner* — Michael Schmitt
(74) *Attorney, Agent, or Firm* — Curatolo Sidoti Co., LPA; Joseph G. Curatolo; Salvatore A. Sidoti

(57) ABSTRACT

Provided are compounds of formula (I)

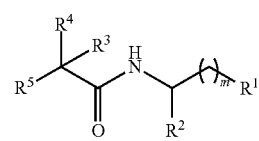

wherein
m is 0, 1 or 2;
$R^1$ is a mono- or bicyclic heterocyclic ring system including one, two or three heteroatoms selected from nitrogen, sulphur and oxygen;
$R^2$ is selected from hydrogen, methyl and ethyl;
I) $R^3$ is hydrogen, methyl, or ethyl; and
$R^4$ and $R^5$ are independently selected from ethyl and isopropyl; and
$R^3$, $R^4$ and $R^5$ together have at least 6 carbon atoms; or
II) any two or all of $R^3$, $R^4$ and $R^5$ form together with the carbon atom to which they are attached 3-para-menthyl, bornyl, or adamantyl;
having cooling properties, their use as cooling agent and compositions including them.

7 Claims, No Drawings

(56) References Cited

FOREIGN PATENT DOCUMENTS

| WO | WO 2006/125334 A1 | 11/2006 |
| WO | WO 2007/019719 A1 | 2/2007 |
| WO | WO 2008/138162 A1 | 11/2008 |
| WO | WO 2008/148234 A1 | 12/2008 |
| WO | WO 2009/012609 A1 | 1/2009 |
| WO | WO 2009/070910 A2 | 6/2009 |
| WO | WO 2009/089641 A1 | 7/2009 |

OTHER PUBLICATIONS

PCT/EP2010/055999—Written Opinion of the International Searching Authority, Jan. 27, 2011.
PCT/EP2010/055999—International Search Report, Jan. 27, 2011.
GB 0910289.8—Great Britain Search Report, Sep. 10, 2009.

* cited by examiner

ORGANIC COMPOUNDS HAVING COOLING PROPERTIES

CROSS REFERENCE TO RELATED APPLICATIONS

This application is a national stage application of International Application No. PCT/EP2010/055999, filed 4 May 2010. which claims priority from U.S. Provisional Patent Application Ser. No. 61/175,513, filed 5 May 2009, from which applications priority is claimed, and which are incorporated herein by reference.

Provided are a new class of compounds having cooling properties. Also provided are a process for their production and consumer products comprising them.

In the flavour and fragrance industry there is an ongoing demand for compounds having unique cooling properties that provide the user with a pleasing cooling effect and which are suitable for use in a variety of products, particularly in ingestible and topically-applied products.

The most well-known cooling compound is I-menthol, which is found naturally in oil of mint. Since menthol has a strong minty odor and a bitter taste, and provides a burning sensation when used in high concentrations, a variety of other menthyl ester-based and menthyl carboxamide-based cooling compounds have been developed. One that has enjoyed substantial success is N-ethyl p-menthane-carboxamide (WS-3) and is thus also often used as a benchmark.

We have now found a novel class of compounds, which is capable of imparting and/or enhancing a physiological cooling effect in a product in which it is incorporated.

Thus there is provided in a first aspect, the use as cooling agent of a compound of formula (I)

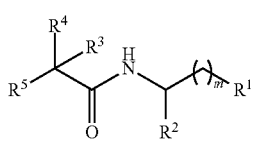

(I)

wherein
m is 0, 1 or 2;
$R^1$ is a mono- or bicyclic heterocyclic ring system comprising one, two or three heteroatoms selected from nitrogen, sulphur and oxygen;
$R^2$ is selected from hydrogen, methyl and ethyl;
I) $R^3$ is hydrogen, methyl, or ethyl; and
  $R^4$ and $R^5$ are independently selected from ethyl and isopropyl; and
  $R^3$, $R^4$ and $R^5$ together comprise at least 6 carbon atoms, e.g. 7, 8 or 9 carbon atoms; or
II) any two or all of $R^3$, $R^4$ and $R^5$ form together with the carbon atom to which they are attached 3-para-menthyl, bornyl, or adamantyl.

As used in relation to compounds of formula (I) unless otherwise indicated "heterocyclic ring system" refers to a monocyclic ring comprising at least one hetero atom, such as furanyl, tetrahydrofuranyl, thiophenyl, triazolyl, e.g. 1H-1,2,4-triazol-1-yl, pyrazolyl, e.g. 1H-pyrazol-1-yl, oxazolyl, thiazolyl, pyrolidinyl, morpholinyl, imidazolyl, e.g. 1H-imidazol-2-yl, pyridinyl, piperidinyl, pyrrolyl, e.g. 1H-pyrrol-2-yl; or bicyclic ring comprising at least one hetero atom, such as indolyl or quinolinyl.

Non limiting examples are compounds of formula (I) wherein $R^3$ is hydrogen and $R^4$ and $R^5$ form together with the carbon atom to which they are attached 2-isopropyl-5-methyl-cyclohex-1-yl, preferable (1R,2S,5R)-2-isopropyl-5-methyl-cyclohex-1-yl, and $R^2$ is hydrogen or methyl.

Further non limited examples are compounds of formula (I) wherein $R^3$ is methyl, $R^4$ and $R^5$ are isopropyl and $R^2$ is hydrogen or methyl.

In particular, embodiments are compounds of formula (I) selected from

N-(1-(furan-2-yl)ethyl)-2-isopropyl-5-methylcyclohexanecarboxamide;

2-isopropyl-5-methyl-N-((1-methyl-1H-pyrrol-2-yl)methyl)cyclohexanecarboxamide;

N-((2,5-dimethylfuran-3-yl)methyl)-2-isopropyl-5-methyl-cyclohexanecarboxamide;

N-((1H-indol-4-yl)methyl)-2-isopropyl-5-methylcyclohexanecarboxamide;

ethyl 5-((2-isopropyl-5-methylcyclohexanecarboxamido)methyl)furan-2-carboxylate;

2-isopropyl-5-methyl-N-(quinolin-3-ylmethyl)cyclohexanecarboxamide;

2-isopropyl-5-methyl-N-(((S)-tetrahydrofuran-2-yl)methyl)cyclohexanecarboxamide;

2-isopropyl-2,3-dimethyl-N-(1-(furan-2-yl)ethyl)butanamide;

2-isopropyl-2,3-dimethyl-N-((1-methyl-1H-pyrrol-2-yl)methyl)butanamide;

(S)-2-isopropyl-2,3-dimethyl-N-((tetrahydrofuran-2-yl)methyl)butanamide;

N-(2-(1H-imidazol-2-yl)ethyl)-2-isopropyl-5-methlycyclohexanecarboxamide;

2-isopropyl-5-methyl-N-(2-(2-methyl-1H-indol-3-yl)ethyl)cyclohexanecarboxamide;

N-(2-(1H-indol-1-yl)ethyl)-2-isopropyl-5-methylcyclohexanecarboxamide;

2-isopropyl-5-methyl-N-(1-(pyridin-3-yl)propan-2-yl)cyclohexanecarboxamide;

2-isopropyl-5-methyl-N-(1-(pyridin-2-yl)propan-2-yl)cyclohexanecarboxamide;

2-isopropyl-5-methyl-N-(2-(6-methyl-1H-indol-3-yl)ethyl)cyclohexanecarboxamide;

2-isopropyl-5-methyl-N-(1-(thiophen-3-yl)propan-2-yl)cyclohexanecarboxamide;

N-(2-(1H-indol-1-yl)ethyl)-2-isopropyl-2,3-dimethylbutanamide;

2-isopropyl-2,3-dimethyl-N-(2-(piperidin-1-yl)ethyl)butanamide;

N-(3-(1H-imidazol-1-yl)propyl)-2-isopropyl-5-methylcyclohexanecarboxamide; and

N-(3-(1H-indol-1-yl)propyl)-2-isopropyl-2,3-dimethylbutanamide.

The compounds of formula (I) may be used in products that are applied to mucous membranes such as oral mucosa, or to the skin, to give a cooling sensation. By "applying" is meant any form of bringing into contact, for example, oral ingestion, topical application or, in the case of tobacco products, inhalation. In the case of application to the skin, it may be, for example, by including the compound in a cream or salve, or in a sprayable composition. There is therefore also provided a method of providing a cooling sensation to the mucous membrane or skin by applying thereto a product comprising an effective amount of a compound as hereinabove described, or mixtures thereof.

Products that are applied to the oral mucosa may include foodstuffs and beverages taken into the mouth and swallowed, and products taken for reasons other than their nutritional value, e.g. tablets, troches, mouthwash, throat sprays, dentifrices and chewing gums, which may be applied to the oral mucosa for the purpose of cleaning, freshening, healing, and/or deodorising.

Products that are applied to the skin may be selected from perfumes, toiletries, cosmetic products such as lotions, oils, ointments and bathing agents, applicable to the skin of the human body, whether for medical or other reasons. Accordingly, in a further aspect there is provided a composition comprising an amount of at least one compound of formula (I) sufficient to stimulate the cold receptors in the areas of the skin or mucous membrane with which the composition comes into contact and thereby promote the desired cooling effect. A cooling effect may be achieved upon application of a product, for example, toothpaste, mouthwash or chewing gum, to the mucous membrane, e.g. oral mucosa, comprising less than 2500 ppm, in certain embodiments between 10 and 500 ppm, such as about 150 ppm, of a compound of formula (I), or mixture thereof. If used for beverages the addition of about 5 ppm may be sufficient to achieve a cooling effect. For use in cosmetic products, the product may comprise from about 50 to about 5000 ppm. However, it is understood that the skilled person may employ compounds of formula (I), as hereinabove described, or a mixture thereof in amounts outside the aforementioned ranges to achieve sensorial effects.

Particular examples of foodstuffs and beverages may include, but are not limited to, beverages, alcoholic or non-alcoholic such as fruit juice beverages, fruit liquors, milk drinks, carbonated beverages, refreshing beverages, and health and nutrient drinks; frozen confectionery such as ice creams and sorbets; desserts such as jelly and pudding; confectionery such as cakes, cookies, chocolates, and chewing gum; jams; candies; breads; tea beverages such as green tea, black tea, chamomile tea, mulberry leaf tea, Roobos tea, peppermint tea; soaps; seasonings; instant beverages: snack foods and the like.

Further examples of products for topical application may include, but are not limited to, skin-care cosmetics such as cleansing tissues, talcum powders, face creams, lotions, tonics and gels; hand creams, hand- and body lotions, anticellulite/slimming creams and -lotions, lotions, balms, gels, sprays and creams; sunburn cosmetics including sunscreen lotions, balms, gels, sprays and creams; after sun lotions, sprays and creams; soaps, toothpicks, lip sticks, agents for bathing, deodorants and antiperspirants, face washing creams, massage creams, and the like, Further examples of products that are applied to the oral mucosa may include, but are not limited to, oral care products such as toothpastes, tooth gels, tooth powders, tooth whitening products, dental floss, anti-plaque and anti-gingivitis compositions, compositions for treatment of nasal symptoms, and gargle compositions.

Thus there is further provided an end-product selected from the group consisting of products that are applied to the oral mucosa and products that are applied to the skin, such as products for topical application, oral care products, nasal care products, toilet articles, ingestible products and chewing gum, and the like which comprises a product base and an effective amount of at least one cooling compound of formula (I) as defined herein above.

The compounds as hereinabove described may be used alone or in combination with other cooling compounds known in the art, e.g. menthol, menthone, isopulegol, N-ethyl p-menthanecarboxamide (WS-3), N,2,3-trimethyl-2-isopropylbutanamide (WS-23), ethyl 2-(2-isopropyl-5methylcyclohexanecarboxamido)-acetate (WS-5), menthyl lactate, menthone glycerine acetal (Frescolat® MGA), mono-menthyl succinate (Physcool®), mono-menthyl glutarate, O-menthyl glycerine (CoolAct® 10) and 2-sec-butylcyclohexanone (Freskomenthe®), menthane, camphor, pulegol, cineol, mint oil, peppermint oil, spearmint oil, eucalyptus oil, 3-l-menthoxypropane-1,2-diol, 3-l-menthoxy-2-methylpropane-1,2-diol, p-menthane-3,8-diol, 2-l-menthoxyethane-1-ol, 3-l-menthoxypropane-1-ol, 4-l-menthoxybutane-1-ol, N,2-diethyl-2-isopropyl-3-methylbutanamide, N-(2-hydroxyethyl)-2-isopropyl-2,3-dimethylbutanamide, 2,2-diethyl-N-(1-hydroxy-2-methylpropan-2-yl)butanamide, and menthyl pyrrolidone carboxcylic acid compounds sold under the commercial name "Questice". Further examples of cooling compounds can be found e.g. in WO 2005/049553 (e.g. 2-isopropyl-5-methyl-cyclohexanecarboxylic acid (4-cyanomethyl-phenyl)-amide and 2-isopropyl-5-methyl-cyclohexanecarboxylic acid (4-cyano-phenyl)-amide), WO2006/125334 (e.g. 4-[(2-isopropyl-5-methyl-cyclohexanecarbonyl)-amino]-benzamide, 3-[(2-isopropyl-5-methyl-cyclohexanecarbonyl)-amino]benzamide, and (2-isopropyl-5-methyl-N-(4-(4-methylpiperazine-1-carbonyl)phenyl) cyclohexanecarboxamide) and WO 2007/019719 (e.g. 2-isopropyl-5-methyl-cyclohexanecarboxylic acid pyridin-2-ylamide, and 2-isopropyl-5-methyl-cyclohexanecarboxylic acid (2-pyridin-2-yl-ethyl)-amide), which are incorporated herein by reference.

Thus there is provided in a further aspect, a composition for cooling comprising a compound of formula (I) as hereinabove defined, or a mixture thereof, optionally combined with at least one other cooling compound.

The cooling compounds of formula (I) may also be blended with known natural sensate compounds, for example, jambu, galangal, galangal acetate, sanshool, capscacian, pepper and ginger, or other flavour and fragrance ingredients generally known to the person skilled in the art. Suitable examples of flavour and fragrance ingredients include alcohols, aldehydes, ketones, esters, ethers, acetates, nitriles, terpene hydrocarbons, nitrogenous, sulphurous heterocyclic compounds, and natural oils, e.g. citrus oil. Flavor and fragrance ingredients may be of natural or synthetic origin. Many of these are listed in reference texts such as the book by S. Arctander, Perfume and Flavor Chemicals, 1969, Montclair, N.J., USA, or its more recent versions.

The cooling compounds may be employed in the products simply by directly mixing the compound with the product, or they may, in an earlier step, be entrapped with an entrapment material such as polymers, capsules, microcapsules and nanocapsules, liposomes, film formers, absorbents such as cyclic oligosaccharides, or they may be chemically bonded to a substrate, which are adapted to release the cooling compound upon application of an external stimulus such as temperature, moisture, and/or enzyme or the like, and then mixed with the product. Or they may be added while being solubilized, dispersed, or diluted using alcohols or polyhydric alcohols, such as, glycerine, propylene glycol, triazethine and mygliol, natural gums such as gum Arabic, or surfactants, such as glycerine fatty acid esters and saccharide fatty acid esters.

The compounds of formula (I) may be prepared by reacting the appropriate acid chloride of the formula $R^3R^4R^5C(O)Cl$ with appropriate amine of the formula $H_2NCHR^2(CH_2)_mR^1$ in the presence of a base (e.g. pyridine triethyl amine, KOH, NaOH) under condition known to the person skilled in the art. $R^1$-$R^5$ and m have the same meaning as defined hereinabove. The amines and chlorides are commercially available and/or the person skilled in the art will know how to synthesize them from other commercially available starting materials.

The compositions and methods are now further described with reference to the following non-limiting examples.

These examples are for the purpose of illustration only and it is understood that variations and modifications can be made by one skilled in the art without departing from the scope of the invention. It should be understood that the embodiments described are not only in the alternative, but can be combined.

EXAMPLE 1

(1R,2S,5R)-2-isopropyl-5-methyl-N-(1-(pyridin-3-yl)propan-2-yl)cyclohexanecarboxamide In a 25 mL round bottom flask, fitted with magnetic stirrer, 15 mL of tetrahydrofuran, 1.5 mmol (1.5 eq.) of pyridine and 1.1 mmol (1.1 eq.) of 1-(pyridin-3-yl)propan-2-amine were added. p-Menthane carboxylic acid chloride (1.0 mmol) and the mixture was stirred at room temperature for 16 hours. The reaction mixture was extracted with MTBE and NaOH (1N in water). The organic layer was washed with brine, dried over $MgSO_4$ and concentrated. The crude product was purified by column chromatography, obtaining 220 mg of a white solid, mp 108-110° C.

$^1$H NMR (300 MHz, DMSO) δ 8.38 (m, 2H), 7.70 (d, 1H), 7.57 (d, 1H), 7.28 (m, 1H), 4.16-3.98 (m, 1H), 2.71-2.61 (m, 2H), 1.95 (q, 1H), 1.66-1.48 (m, 3H), 1.33-0.78 (m, 14H), 0.72-0.53 (m, 4H).

Example 2A to 2N

The following compounds were prepared following the general procedure as described in Example 1.

2A: (1R,2S,5R)-N-(1-(furan-2-yl)ethyl)-2-isopropyl-5-methylcyclohexanecarboxamide

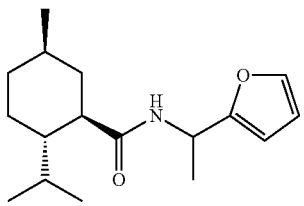 [SMILES: CC(NC(=O)[C@@H]1C[C@H](C)CC[C@H]1C(C)C)c1ccco1]

$^1$H NMR (300 MHz, CDCl$_3$) δ 7.34 (m, 1H), 6.30 (m, 1H), 6.16 (m, 1H), 5.62 (s, 1H), 5.24 (m, 1H), 1.97 (m, 1H), 1.79-1.64 (m, 4H), 1.53-1.45 (m, 4H), 1.30-1.21 (m, 2H), 1.02-0.87 (m, 8H), 0.76 (m, 3H).

2B: (1R,2S,5R)-2-isopropyl-5-methyl-N-((1-methyl-1H-pyrrol-2-yl)methyl)cyclohexane-carboxamide

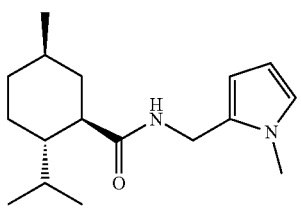 [SMILES: CC(C)[C@@H]1CC[C@@H](C)C[C@H]1C(=O)NCc1cccn1C]

$^1$H NMR (300 MHz, DMSO) δ: 8.08 (s, 1H), 6.65 (s, 1H), 5.84 (s, 2H), 4.27-4.11 (d, 2H), 3.49 (s, 3H), 2.22-2.06 (m, 1H), 1.78-1.20 (m, 7H), 1.18-0.91 (m, 2H), 0.86-0.79 (t, 7H), 0.77-0.69 (d, 3H). LC-MS: 277.3 (M$^+$), 299.3 (M$^{+23}$).

2C: (1R,2S,5R)-N-((2,5-dimethylfuran-3-yl)methyl)-2-isopropyl-5-methylcyclohexane-carboxamide

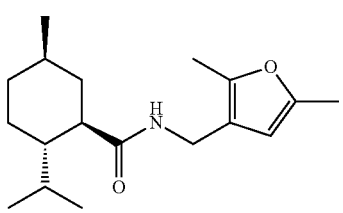 [SMILES: Cc1cc(CNC(=O)[C@@H]2C[C@H](C)CC[C@H]2C(C)C)c(C)o1]

$^1$H NMR (300 MHz, CDCl$_3$) δ: 8.07-7.98 (t, 1H), 5.85 (s, 1H), 3.99-3.89 (t, 2H), 2.18-2.01 (m, 7H), 1.74-1.51 (m, 4H), 1.48-1.22 (m, 2H), 1.17-0.88 (m, 9H), 0.77-0.67 (d, 3H). LC-MS: 292.2 (M$^+$), 314.2 (M$^{+23}$).

2D: (1R,2S,5R)-N-((1H-indol-4-yl)methyl)-2-isopropyl-5-methylcyclohexanecarboxamide;

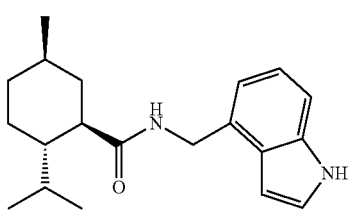 [SMILES: CC(C)[C@@H]1CC[C@@H](C)C[C@H]1C(=O)NCc1cccc2[nH]ccc12]

$^1$H NMR (300 MHz, DMSO) δ 11.1 (s, 1H), 8.26 (t, 1H), 7.30 (m, 2H), 7.03 (t, 1H), 6.85 (d, 1H), 6.48 (s, 1H), 4.51 (qd, 2H), 2.19 (m, 1H), 1.69 (m, 4H), 1.45 (m, 1H), 1.15 (m, 1H), 1.10-0.82 (m, 9H), 0.75 (d, 3H).

-continued

2E: ethyl 5-(((1R,2S,5R)-2-isopropyl-5-methylcyclohexane-carboxamido)methyl)furan-2-carboxylate;

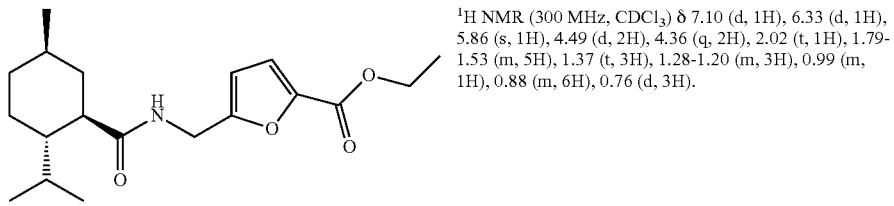

$^1$H NMR (300 MHz, CDCl$_3$) δ 7.10 (d, 1H), 6.33 (d, 1H), 5.86 (s, 1H), 4.49 (d, 2H), 4.36 (q, 2H), 2.02 (t, 1H), 1.79-1.53 (m, 5H), 1.37 (t, 3H), 1.28-1.20 (m, 3H), 0.99 (m, 1H), 0.88 (m, 6H), 0.76 (d, 3H).

2F: (1R,2S,5R)-2-isopropyl-5-methyl-N-(quinolin-3-ylmethyl)cyclohexanecarboxamide;

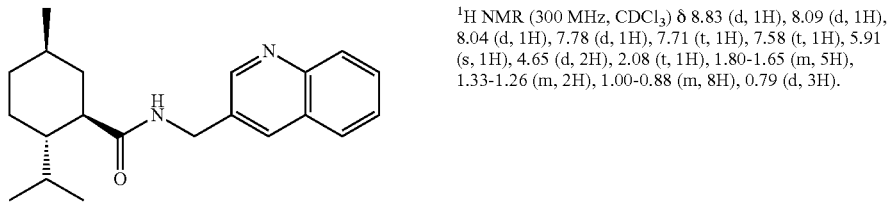

$^1$H NMR (300 MHz, CDCl$_3$) δ 8.83 (d, 1H), 8.09 (d, 1H), 8.04 (d, 1H), 7.78 (d, 1H), 7.71 (t, 1H), 7.58 (t, 1H), 5.91 (s, 1H), 4.65 (d, 2H), 2.08 (t, 1H), 1.80-1.65 (m, 5H), 1.33-1.26 (m, 2H), 1.00-0.88 (m, 8H), 0.79 (d, 3H).

2G: (1R,2S,5R)-2-isopropyl-5-methyl-N-(((S)-tetrahydrofuran-2-yl)methyl)cyclohexane-carboxamide

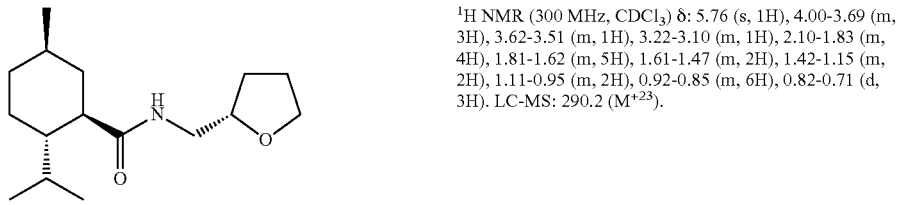

$^1$H NMR (300 MHz, CDCl$_3$) δ: 5.76 (s, 1H), 4.00-3.69 (m, 3H), 3.62-3.51 (m, 1H), 3.22-3.10 (m, 1H), 2.10-1.83 (m, 4H), 1.81-1.62 (m, 5H), 1.61-1.47 (m, 2H), 1.42-1.15 (m, 2H), 1.11-0.95 (m, 2H), 0.92-0.85 (m, 6H), 0.82-0.71 (d, 3H). LC-MS: 290.2 (M$^{+23}$).

2H: (1R,2S,5R)-N-(2-(1H-imidazol-2-yl)ethyl)-2-isopropyl-5-methlycyclohexane-carboxamide

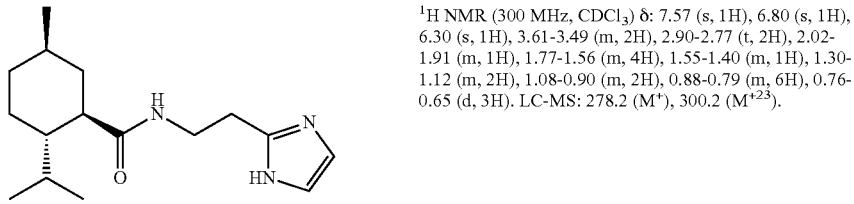

$^1$H NMR (300 MHz, CDCl$_3$) δ: 7.57 (s, 1H), 6.80 (s, 1H), 6.30 (s, 1H), 3.61-3.49 (m, 2H), 2.90-2.77 (t, 2H), 2.02-1.91 (m, 1H), 1.77-1.56 (m, 4H), 1.55-1.40 (m, 1H), 1.30-1.12 (m, 2H), 1.08-0.90 (m, 2H), 0.88-0.79 (m, 6H), 0.76-0.65 (d, 3H). LC-MS: 278.2 (M$^+$), 300.2 (M$^{+23}$).

2I: (1R,2S,5R)-2-isopropyl-5-methyl-N-(2-(2-methyl-1H-indol-3-yl)ethyl)cyclohexane-carboxamide

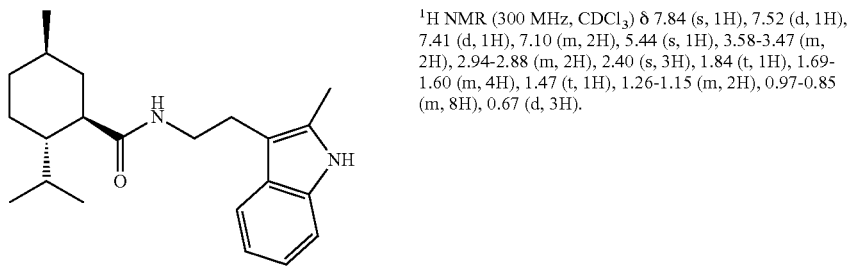

$^1$H NMR (300 MHz, CDCl$_3$) δ 7.84 (s, 1H), 7.52 (d, 1H), 7.41 (d, 1H), 7.10 (m, 2H), 5.44 (s, 1H), 3.58-3.47 (m, 2H), 2.94-2.88 (m, 2H), 2.40 (s, 3H), 1.84 (t, 1H), 1.69-1.60 (m, 4H), 1.47 (t, 1H), 1.26-1.15 (m, 2H), 0.97-0.85 (m, 8H), 0.67 (d, 3H).

2J: (1R,2S,5R)-N-(2-(1H-indol-1-yl)ethyl)-2-isopropyl-5-methylcyclohexanecarboxamide

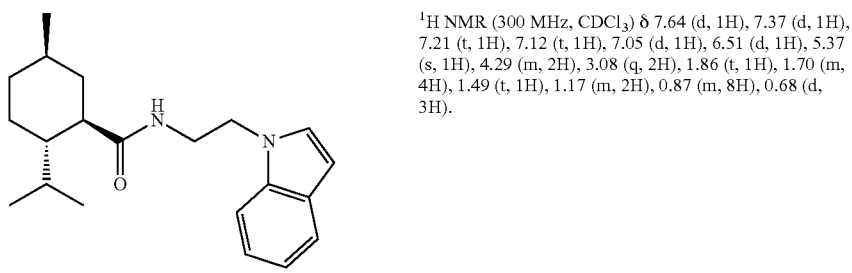

$^1$H NMR (300 MHz, CDCl$_3$) δ 7.64 (d, 1H), 7.37 (d, 1H), 7.21 (t, 1H), 7.12 (t, 1H), 7.05 (d, 1H), 6.51 (d, 1H), 5.37 (s, 1H), 4.29 (m, 2H), 3.08 (q, 2H), 1.86 (t, 1H), 1.70 (m, 4H), 1.49 (t, 1H), 1.17 (m, 2H), 0.87 (m, 8H), 0.68 (d, 3H).

-continued

2K: (1R,2S,5R)-2-isopropyl-5-methyl-N-(1-(pyridin-2-yl)propan-2-yl)cyclohexane-carboxamide

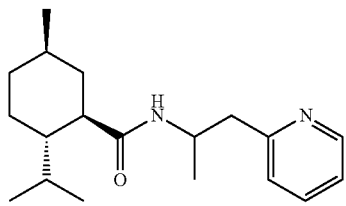 [SMILES: CC(Cc1ccccn1)NC(=O)[C@@H]1C[C@H](C)CC[C@H]1C(C)C]

$^1$H NMR (300 MHz, MeOD) δ 8.43 (d, 1H), 7.89 (d, 1H), 7.73 (m, 1H), 7.33 (d, 1H), 7.25 (dd, 1H), 4.43-4.36 (m, 1H), 2.97-2.83 (m, 2H), 2.07-1.98 (m, 1H), 1.73-1.61 (m, 3H), 1.59-1.40 (m, 2H), 1.19-1.00 (m, 5H), 0.99-0.83 (m, 6H), 0.75 (m, 3H), 0.59 (d, 2H).

2L: (1R,2S,5R)-2-isopropyl-5-methyl-N-(2-(6-methyl-1H-indol-3-yl)ethyl)cyclohexane-carboxamide

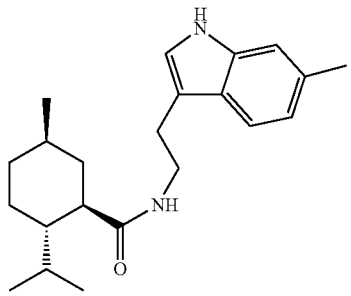 [SMILES: Cc1ccc2c(CCNC(=O)[C@@H]3C[C@H](C)CC[C@H]3C(C)C)c[nH]c2c1]

$^1$H NMR (300 MHz, CDCl$_3$) δ 7.94 (s, 1H), 7.40 (s, 1H), 7.28 (d, 1H), 7.05 (m, 1H), 6.99 (d, 1H), 5.44 (s, 1H), 3.61 (m, 2H), 2.94 (m, 2H), 2.46 (s, 3H), 1.86 (m, 1H), 1.72-1.61 (m, 4H), 1.48 (m, 1H), 1.25-1.18 (m, 2H), 0.93-0.85 (m, 8H), 0.67 (d, 3H).

2M: (1R,2S,5R)-2-isopropyl-5-methyl-N-(1-(thiophen-3-yl)propan-2-yl)cyclohexane-carboxamide

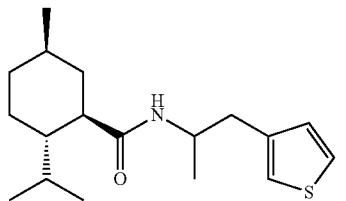 [SMILES: CC(Cc1ccsc1)NC(=O)[C@@H]1C[C@H](C)CC[C@H]1C(C)C]

$^1$H NMR (300 MHz, CDCl$_3$) δ 7.16 (m, 1H), 6.95 (m, 1H), 6.82 (d, 1H), 5.27 (s, 1H), 4.31 (m, 1H), 3.02-2.98 (m, 2H), 1.93-1.89 (m, 1H), 1.74-1.59 (m, 4H), 1.49 (t, 1H), 1.40-1.14 (m, 5H), 0.97-0.85 (m, 8H), 0.72 (m, 3H).

2N: (1R,2S,5R)-N-(3-(1H-imidazol-1-yl)propyl)-2-isopropyl-5-methylcyclohexane-carboxamide

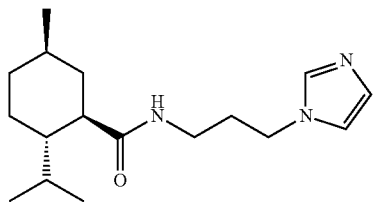 [SMILES: CC(C)[C@@H]1CC[C@@H](C)C[C@H]1C(=O)NCCCn1ccnc1]

$^1$H NMR (300 MHz, CDCl$_3$) δ: 7.56 (s, 1H), 7.08 (s, 1H), 6.97 (s, 1H), 5.72 (s, 1H), 4.07-3.92 (t, 2H), 1.39-3.16 (m, 2H), 2.13-1.87 (m, 5H), 1.81-1.60 (m, 4H), 1.59-1.48 (m, 1H), 1.45-1.15 (m, 2H), 1.09-0.96 (m, 2H), 0.93-0.88 (t, 6H), 0.84-0.66 (d, 3H).
LC-MS: 292.2 (M$^+$), 314.2 (M$^{+23}$).

EXAMPLE 3

2-isopropyl-2,3-dimethyl-N-(1-(furan-2-yl)ethyl)butanamide

In a 25 mL round bottom flask, fitted with magnetic stirrer, 15 mL of tetrahydrofuran, 2.1 mmol (1.5 eq.) of pyridine and 1.54 mmol (1.1 eq.) of 1-(furan-2-yl)ethanamine were added. 1.4 mmol of 2-isopropyl-2,3-dimethylbutanoyl chloride (prepared by hydrolysis of 2-isopropyl-N,2,3-trimethylbutanamide, WS-23 with NaNO$_2$ in H$_2$SO$_4$ and subsequent acid chloride formation with SOCl$_2$) were added and the mixture was stirred at room to temperature for 16 hours, overnight. The reaction mixture was extracted with MTBE and HCl (1N in water). The organic layer was washed with NaOH (1N in water) and brine, dried over MgSO$_4$ and concentrated. The crude product was purified by column chromatography, obtaining 160 mg of a beige solid, mp 57-60° C.

$^1$H NMR (300 MHz, DMSO) δ 7.53 (d, 1H), 7.34 (d, 1H), 6.36 (m, 1H), 6.17 (m, 1H), 5.14 (m, 1H), 1.94 (m, 2H), 1.37 (d, 3H), 0.93 (s, 3H), 0.83-0.76 (m, 12H).

Example 4A to 4E

The following compounds were prepared following the general procedure as described in Example 3.

4A: 2-isopropyl-2,3-dimethyl-N-((1-methyl-1H-pyrrol-2-yl)methyl)butanamide

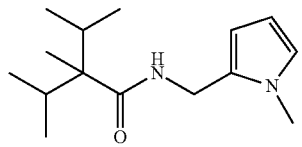 [SMILES: CC(C)C(C)(C(=O)NCc1cccn1C)C(C)C]

$^1$H NMR (300 MHz, CDCl$_3$) δ: 6.65-6.58 (t, 1H), 6.11-6.04 (t, 2H), 5.58 (s, 1H), 4.48-4.39 (d, 2H), 3.57 (s, 3H), 2.10-1.95 (m, 2H), 0.98 (s, 3H), 0.95-0.90 (d, 6H), 0.89-0.81 (d, 6H). LC-MS: 273.2 (M$^{+23}$).

4B: (S)-2-isopropyl-2,3-dimethyl-N-((tetrahydrofuran-2-yl)methyl)butanamide

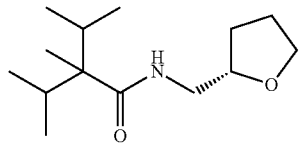 [SMILES: CC(C)C(C)(C(=O)NC[C@@H]1CCCO1)C(C)C]

$^1$H NMR (300 MHz, CDCl$_3$) δ: 5.97 (s, 1H), 4.02-3.91 (m, 1H), 3.90-3.70 (m, 2H), 3.68-3.47 (m, 1H), 3.21-3.07 (m, 1H), 2.11-1.82 (m, 5H), 1.01 (s, 3H), 0.98-0.91 (d, 6H), 0.90-0.81 (d, 6H).
LC-MS: 242.4 (M), 264.3 (M + 22).

4C: N-(2-(1H-indol-1-yl)ethyl)-2-isopropyl-2,3-dimethylbutanamide

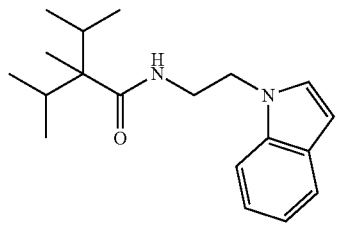 [SMILES: CC(C)C(C)(C(=O)NCCn1ccc2ccccc21)C(C)C]

$^1$H NMR (300 MHz, CDCl$_3$) δ: 7.70-7.61 (d, 1H), 7.47-7.35 (d, 1H), 7.23-7.02 (m, 3H), 6.50 (s, 1H), 5.58 (s, 1H), 4.32-4.23 (t, 2H), 3.74-3.61 (m, 2H), 2.10-1.89 (m, 2H), 0.91 (s, 3H), 0.88-0.84 (d, 6H), 0.82-0.77 (d, 6H).
LC-MS: 323.2 (M$^{+23}$).

4D: 2-isopropyl-2,3-dimethyl-N-(2-(piperidin-1-yl)ethyl)butanamide

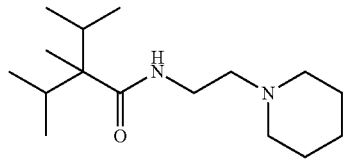 [SMILES: CC(C)C(C)(C(=O)NCCN1CCCCC1)C(C)C]

$^1$H NMR (300 MHz, DMSO) δ: 7.09 (s, 1H), 3.26-3.11 (m, 2H), 2.38 (s, 4H), 2.00-1.82 (m, 2H), 1.57-1.25 (m, 6H), 0.90 (s, 3H), 0.85-0.71 (t, 12H).
LC-MS: 269.4 (M$^+$).

4E: N-(3-(1H-indol-1-yl)propyl)-2-isopropyl-2,3-dimethylbutanamide

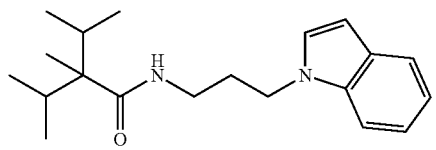 [SMILES: CC(C)C(C)(C(=O)NCCCn1ccc2ccccc21)C(C)C]

$^1$H NMR (300 MHz, CDCl$_3$) δ: 7.70-7.60 (d, 1H), 7.41-7.31 (d, 1H), 7.23-7.16 (m, 1H), 7.13-7.02 (m, 2H), 6.51 (s, 1H), 5.47 (s, 1H), 4.28-4.17 (t, 2H), 3.35-3.20 (m, 2H), 2.16-2.01 (m, 2H), 2.00-1.86 (m, 2H), 0.88 (s, 3H), 0.86-0.82 (d, 6H), 0.80-0.75 (d, 6H).
LC-MS: 337.3 (M$^{+23}$).

EXAMPLE 5

Cooling Intensity

A small group of panelists was asked to taste various aqueous solutions of compounds of formula (I) and indicate which solutions had a cooling intensity similar to or slightly higher than that of a solution of menthol at 2 ppm. The results are shown in Table 3.

TABLE 3

| Compound | Concentration |
|---|---|
| Comparison: l-Menthol | 2.0 ppm |
| Comparison: N-ethyl p-menthanecarboxamide | 1.5 ppm |
| Comparison: (1R,2S,5R)-N-(4-(cyanomethyl)phenyl)-2-isopropyl-5-methylcyclohexanecarboxamide | 0.2 ppm |
| Comparison: (1R,2S,5R)-2-isopropyl-5-methyl-N-(2-(pyridin-2-yl)ethyl)cyclohexanecarboxamide | 0.02 ppm |
| (1R,2S,5R)-N-(2-(1H-imidazol-2-yl)ethyl)-2-isopropyl-5-methylcyclohexanecarboxamide (Example 2H) | 0.2 ppm |
| (1R,2S,5R)-2-isopropyl-5-methyl-N-(1-(thiophen-3-yl)propan-2-yl)cyclohexanecarboxamide (Example 2M) | 0.002 ppm |
| (1R,2S,5R)-2-isopropyl-5-methyl-N-(1-(pyridin-3-yl)propan-2-yl)cyclohexanecarboxamide (Example 1) | 0.01 ppm |
| (1R,2S,5R)-2-isopropyl-5-methyl-N-(2-(2-methyl-1H-indol-3-yl)ethyl)cyclohexanecarboxamide (Example 2J) | 0.002 ppm |

EXAMPLE 6

Application in Toothpaste 0.10 g of a 10% solution in ethanol of a compound of formula (I) listed in Table 4 below and 0.03 g saccharin were mixed in 9.96 g of an opaque toothgel base.

A piece of the thus prepared toothpaste was put on a toothbrush and a panelist's teeth were brushed. The mouth was rinsed with water and the water spat out. A long lasting cooling sensation was felt by the panelist in all areas of the mouth. The cooling sensation was perceived for up to 60 min (see Table 5).

TABLE 5

Cooling sensation

| Compound | Perceived cooling sensation |
|---|---|
| (1R,2S,5R)-2-isopropyl-5-methyl-N-(2-(2-methyl-1H-indol-3-yl)ethyl)cyclohexane-carboxamide (Example 2I) | 60 min |
| (1R,2S,5R)-2-isopropyl-5-methyl-N-(1-(thiophen-3-yl)propan-2-yl)cyclohexane-carboxamide (Example 2M) | 40 min |
| (1R,2S,5R)-2-isopropyl-5-methyl-N-(1-(pyridin-3-yl)propan-2-yl)cyclohexanecarboxamide (Example 1) | 30 min |
| (1R,2S,5R)-N-(2-(1H-imidazol-2-yl)ethyl)-2-isopropyl-5-methlycyclohexane-carboxamide (Example 2H) | 40 min |

The invention claimed is:

1. A method of providing a cooling sensation to the skin or mucosa membrane by applying thereto a compound selected from the group consisting of
   2-isopropyl-5-methyl-N-(2-(2-methyl-1H-indol-3-yl) ethyl)cyclohexanecarboxamide;
   N-(2-(1H-indol-1-yl)ethyl)-2-isopropyl-5-methylcyclohexanecarboxamide; and
   2-isopropyl-5-methyl-N-(2-(6-methyl-1H-indol-3-yl) ethyl)cyclohexanecarboxamide.

2. A composition for cooling comprising
   a flavor ingredient and/or an other cooling compound; and
   at least one compound selected from the group consisting of
   2-isopropyl-5-methyl-N-(2-(2-methyl-1H-indol-3-yl) ethyl)cyclohexanecarboxamide;
   N-(2-(1H-indol-1-yl)ethyl)-2-isopropyl-5-methylcyclohexanecarboxamide; and
   2-isopropyl-5-methyl-N-(2-(6-methyl-1H-indol-3-yl) ethyl)cyclohexanecarboxamide.

3. A composition according to claim 2 wherein the other cooling compound is selected from the group consisting of menthol, menthone, isopulegol, N-ethyl p-menthanecarboxamide, N,2,3-trimethyl-2-isopropylbutanamide, ethyl 2-(2-isopropyl-5methylcyclohexanecarboxamido)-acetate, menthyl lactate, menthone glycerine acetal, mono-menthyl succinate, mono-menthyl glutarate, O-menthyl glycerine, 2-sec-butylcyclohexanone, menthane, camphor, pulegol, cineol, mint oil, peppermint oil, spearmint oil, eucalyptus oil, 3-l-menthoxypropane-1,2-diol, 3-l-menthoxy-2-methylpropane-1,2-diol, p-menthane-3,8-diol, 2-l-menthoxyethane-1-ol, 3-l-menthoxypropane-1-ol, 4-l-menthoxybutane-1-ol, N,2-diethyl-2-isopropyl-3-methylbutanamide, N-(2-hydroxyethyl)-2-isopropyl-2,3-dimethylbutanamide, 2,2-diethyl-N-(1-hydroxy-2-methylpropan-2-yl)butanamide, menthyl pyrrolidone carboxylic acid, 2-isopropyl-5-methyl-cyclohexanecarboxylic acid (4-cyanomethyl-phenyl)-amide, 2-isopropyl-5-methyl-cyclohexanecarboxylic acid (4-cyano-phenyl)-amide), 4-[(2-isopropyl-5-methyl-cyclohexanecarbonyl)-amino]-benzamide, 3-[(2-isopropyl-5-methyl-cyclohexanecarbonyl)-amino]benzamide, (2-isopropyl-5-methyl-N-(4-(4-methylpiperazine-1-carbonyl)phenyl) cyclohexanecarboxamide), 2-isopropyl-5-methyl-cyclohexanecarboxylic acid pyridin-2-ylamide, and 2-isopropyl-5-methyl-cyclohexanecarboxylic acid (2-pyridin-2-yl-ethyl)-amide).

4. A composition according to claim 2 further comprising a solvent is selected from the group consisting of glycerine, propylene glycol, triazethine, and mygliol.

5. A product adapted to be applied to the oral mucosa or to the skin, comprising a product base and an effective amount of at least one compound selected from the group consisting of
   2-isopropyl-5-methyl-N-(2-(2-methyl-1H-indol-3-yl) ethyl)cyclohexanecarboxamide;
   N-(2-(1H-indol-1-yl)ethyl)-2-isopropyl-5-methylcyclohexanecarboxamide; and
   2-isopropyl-5-methyl-N-(2-(6-methyl-1H-indol-3-yl) ethyl)cyclohexanecarboxamide.

6. A method of using a compound selected from the group consisting of
   2-isopropyl-5-methyl-N-(2-(2-methyl-1H-indol-3-yl) ethyl)cyclohexanecarboxamide;
   N-(2-(1H-indol-1-yl)ethyl)-2-isopropyl-5-methylcyclohexanecarboxamide; and
   2-isopropyl-5-methyl-N-(2-(6-methyl-1H-indol-3-yl) ethyl)cyclohexanecarboxamide;
   as a cooling agent comprising employing an effective amount of at least one compound from the group in a product adapted to be applied to mucous membrane or to the skin to give a cooling sensation.

7. The method of claim 6 comprising (i) directly mixing the compound with the product, (ii) entrapping the compound with an entrapment material or chemically bonding the compound to a substrate adapted to release the compound upon application of an external stimulus, and then mixing with the product, or (iii) adding the compound to the product while being solubilized, dispersed, or diluted using alcohol, polyhydric alcohol, natural gum, or surfactant.

* * * * *